United States Patent [19]

Vahlne et al.

[11] Patent Number: 5,017,687

[45] Date of Patent: May 21, 1991

[54] PEPTIDES FOR THE DETECTION OF HTLV-1 INFECTION

[75] Inventors: Anders Vahlne, Hovas; Bo Svennerholm, Gothenburg; Lars Rymo, Hovas; Stig Jeansson; Peter Horal, both of Gothenburg, all of Sweden

[73] Assignee: Virovahl, S.A., Zug, Switzerland

[21] Appl. No.: 206,140

[22] Filed: Jun. 13, 1988

Related U.S. Application Data

[63] Continuation-in-part of Ser. No. 166,205, Mar. 10, 1988, abandoned.

[51] Int. Cl.$^5$ .......................... C07K 7/10; C07K 17/00
[52] U.S. Cl. .................................... 530/324; 530/325; 530/326; 424/86; 424/89; 514/12; 435/5
[58] Field of Search ................... 530/324, 7, 325, 326; 424/86, 89; 514/12

[56] References Cited

U.S. PATENT DOCUMENTS

| | | |
|---|---|---|
| 4,722,888 | 2/1988 | Broder et al. |
| 4,735,896 | 4/1988 | Wang et al. |
| 4,753,873 | 6/1988 | Beltz et al. |
| 4,757,000 | 7/1988 | Tohmatsu et al. |

FOREIGN PATENT DOCUMENTS

| | | |
|---|---|---|
| 0152030 | 8/1985 | European Pat. Off. |
| 0214555 | 3/1987 | European Pat. Off. |
| 0246101 | 8/1987 | European Pat. Off. |

OTHER PUBLICATIONS

Patent Abstract of Japan, vol. 9, No. 306 (C-317) JP 60-142925 published, Jul. 29, 1985.
Patent Abstract of Japan, vol. 9, No. 145 (C-287) JP 60-28993 published Feb. 14, 1985.
Cianciolo et al., "Inhibition of Lymphocyte Proliferation by a Synthetic Peptide Homologous to Retroviral Envelope Proteins", Science 230:453-455.
Seiki, PNAS (6/1983) 80:3618-3622.
Copeland, J. Immunology (Nov. 1, 1986) 137:2945-2951.
Dialog Accession No. 89-082937/11, "Antigen for Detection of Antibody Against HTLV-1 Used in Peptide Compsn. for Vaccine Against ATL".
Dialog Accession No. 88169913, Parker et al., "Purification of Human Lymphotropic Virus Type I (HTLV-I) by Affinity Chromatography", J. Virol. Met. (1987) 18:243-255.
Dialog Accession no. 86064177, Blomberg et al., "Immunoglobulin G ANtiobodies Binding to a Synthetic Peptide Deduced from the Nucleotide Sequence of the env gene of HTLV-1 in Patients with Leukemia and Rheumatoid Arthritis, HLA Sensitized Persons and Blood Donors", Leuk. Res. (1985) 9:1111-1116.
Dialog Accession No. 84276010, Hattori et al., "Identification of gag and env Gene Products of Human T cell Leukemia Virus (HTLV)", Virol. (1984) 136:338-347.

*Primary Examiner*—Margaret Moskowitz
*Assistant Examiner*—D. Bernstein
*Attorney, Agent, or Firm*—Brumbaugh, Graves, Donohue & Raymond

[57] ABSTRACT

Four peptides corresponding to regions of the glycoprotein encoded by the env gene of HTLV1 are provided. These peptides which are immunologically reactive with HTLV-1 specific antibodies are useful in assays for detection of HTLV-1 infection or exposure and in compositions to elicit the production of antibodies against HTLV-1 in animals and man.

26 Claims, No Drawings

PEPTIDES FOR THE DETECTION OF HTLV-1 INFECTION

The present application is a continuation-in-part of U.S. patent application Ser. No. 07/166,255 filed Mar. 10, 1988 abandoned.

BACKGROUND OF THE INVENTION

The present invention relates to synthetic peptides, the sequences of which correspond to antigenic regions of an immunologically important protein of HTLV-1. These peptides are useful as diagnostic reagents for detecting the presence of antibodies to HTLV-1 and may also be useful as immunogens in compositions and methods to elicit antibodies against HTLV-1 in animals and man.

The etiologic agent of adult T-cell leukemia/lymphoma (ATL) has been identified as HTLV-1 (human T-cell lymphotropic virus type 1). See e.g., Sarngadharan et al., in *Virology* (1985) B. N. Fields et al., eds., pp. 1345-1371, for a review. The region of the world where the virus is most prevalent is the island of Kyushu in southern Japan where about 15% of the population has been infected. Recently a tropical paralysis called tropical spastic paraparesis (TSP) has also been associated with HTLV-1 infection. Rodgers-Johnson et al., Lancet (1985) II:1247; Vernant et al., Ann. Neurol (1987) 21:123. In the tropics TSP is of the same magnitude and importance as the multiple sclerosis syndrome is in the western world. Marx, Science (1987) 236:1059-1061.

Methods for detection of HTLV-1 infection, in general, measure exposure to the virus by detecting and quantifying antibodies to HTLV-1 antigens in blood, sera, and blood-derived products. Such assays can be used to aid diagnosis of ATL and TSP and to screen blood and blood products for previous exposure to HTLV-1.

The current attempts to diagnose HTLV-1 infections and screen blood for exposure to HTLV-1 include enzyme-linked immunosorbent assay (ELISA) techniques to detect the presence of antibodies to immunogenic components of HTLV-1 in a test sample. Other methods may utilize Western blotting techniques to detect HTLV-1 specific antibodies in test samples. In general, almost any known immunoassay, such as radioimmunoassays, agglutination tests or indirect immunofluorescence, in addition to ELISA and Western blots, can be adapted, by use of specific reagents, for the detection of HTLV-1 and antibodies thereto.

The source of antigens for these assays may include inter alia antigenic proteins obtained from HTLV-1 infected T cell lines and antigens produced by recombinant DNA techniques. The use of antigens obtained from these sources, however, has significant drawbacks.

The production of HTLV-1 per se in continuous cell lines must be performed in high risk (P3 containment) laboratories due to the danger to investigators who may become adversely exposed to the virus. It is also likely that the use of T cell derived HTLV-1 antigens can produce false negative and false positive results in ELISA tests. For example, by analogy, in measuring exposure to the AIDS virus, there have been false negative and false positive results reported with ELISA tests using whole virus HIV-1 antigens obtained from cell lines. Gurtler et al., J Virological Methods (1987) 15:11-23. Western blot analyses for HTLV-1 detection, using electroblotted whole virus antigens, should provide greater specificity but are more laborious and time-consuming than ELISA tests. Furthermore, since HTLV-1 producing cells are of human origin, viral antigen preparations obtained from these cell lines, unless exhaustively purified, may be contaminated with normal cellular antigens, such as HLA antigens, which could produce false positive reactions in a ELISA test.

Exhaustive purification of viral antigens from cell lines can also conceivably destroy immunogenicity of immunologically important proteins or otherwise inactivate antigens, thereby producing reagents that result in false negative reactions. In addition, false negative reactions using live-virus-derived antigens may occur because of steric hindrance whereby antibodies cannot react with their specific antigens because the reaction is blocked by the presence of other antigens and antibodies in the reaction mixture.

ELISA tests to detect HTLV-1 infection may also employ immunologically important viral proteins produced by cloning portions of the HTLV-1 genome in bacteria. The complete nucleotide sequence of HTLV-1 has been reported by Seiki et al., Proc. Natl. Acad. Sci. U.S.A. (1983) 80:3618-3622. The viral envelope glycoproteins and core proteins, respectively encoded by the env and gag genes of HTLV-1, are apparently the antigens recognized by antibodies in the sera of patients with HTLV-1 infection.

Immunologically important HTLV-1 antigens, which are present in the viral envelope and core, may be prepared by cloning portions of the HTLV-1 genome in various expression systems such as bacteria, yeast or vaccinia. Such recombinant antigens may be used in diagnosis and as potential vaccine compositions as has been done for HIV-1 proteins. See, e.g. Cabradilla et al., Biotechnology (1986) 4:128-133; Chang et al., Biotechnology (1985) 3:905-909; Putney et al., Science (1986) 234:1392-1395; Kieny et al. Biotechnology (1986) 4:790-795. HTLV-1 antigens produced by recombinant DNA methods, however, must still be exhaustively purified to avoid false positive reactions in the ELISA due to any antibody reactivity to antigens of the expression system which may contaminate the HTLV-1 antigen preparation. Also, denaturation of HTLV-1 antigens during purification may destroy important antigen activity.

While HTLV-1 antigens produced by recombinant techniques may be an improvement over antigens obtained from virus-infected cell cultures, the recombinant proteins still may not provide reagents that give as accurate a diagnosis as possible. Because of the nature of the disease and the need for accurate results, other reagents must be developed to approach 100% accuracy in diagnosis of HTLV-1.

Proteins contain a number of epitopes or antigenic determinants which are the regions of the proteins which comprise the binding sites for specific antibodies. In general, proteins contain between 5 to 10 epitopes, each of which comprises a sequence of 6 to 8 amino acids. Epitopes can be either continuous, in which the 6 to 8 amino acids are present in linear sequence, or discontinuous, in which case the amino acids that form the epitope are brought together by the three dimensional folding of the protein. Even though an epitope constitutes only a relatively few amino acids, its reactivity with an antibody is influenced by the amino acids in the protein which surround the epitope.

Studies aimed at mapping antigenic sites or epitopes of proteins have been aided by the use of synthetic peptides corresponding to various regions of the proteins of interest. See, e.g., Lerner et al., in *The Biology of Immunological Disease: A Hospital Practice Book*, (1983) Dixon and Fisher, eds., pp. 331-338; Lerner, *Adv. Immunol.* (1984) 36:1. In addition to their usefulness in epitope mapping studies, synthetic peptides, if encompassing major antigenic determinants of a protein, have potential as immunogenic compositions, including vaccines and diagnostic reagents. Synthetic peptide antigens have several advantages in specific antibody production and reactivity. The exact sequence of the peptide can be selected from the amino acid sequence as actually determined by amino acid sequencing of a protein or predicted from the DNA sequence coding for the protein. The use of specific synthetic peptides eliminates the need for using the full-length protein in the production of or assay for specific antibodies. Furthermore, the solid phase peptide synthetic techniques of Merrifield and coworkers allow for essentially unlimited quantities of the synthesized peptide of interest to be chemically produced. See, e.g., Erickson and Merrifield in *The Proteins*, 3rd Edit. (1976), Vol 2, Academic Press, New York, Chapter 3. The availability of automated peptide synthesizers has further advanced such techniques.

Although a variety of criteria can be used to determine which regions of proteins are immunodominant, peptides corresponding to such regions may not always be useful in large-scale screening and diagnosis for example, antigenicity may be lost because the peptide is not in a proper spatial orientation which is recognized by antibodies which react with the protein. Furthermore, as is particularly evident with HIV-I and HIV-2, there is significant genetic variability within each of these two virus groups leading to many serotypes of the viruses. This has put a significant constraint on choosing a region of a protein from which to derive a peptide for use in screening and diagnosis and in formulating vaccines. However, certain immunodominant portions of HIV-1 and HIV-2 proteins have been found to be relatively invariant. It is believed that useful synthetic peptides may be derived from such protein regions.

Recently, such immunologically reactive peptides corresponding to various immunodominant regions of the surface glycoproteins gp120 and gp41 from HIV-1 and the corresponding proteins of HIV-2 encoded by the env gene of the two viruses have been synthesized and shown to react with about 100% efficiency with sera from HIV-1 or HIV-2 infected individuals. When used in assays for detecting the presence of antibodies, such peptides gave no false positive or false negative reactions. See e.g. U.S. patent application Ser. Nos. 051,726 and 051,727 both filed May 18, 1987.

It is believed that a similar approach for diagnosis of HTLV-1 infection using synthetic peptides derived from immunologically important proteins of HTLV-1 would be extremely useful especially in those areas of the world where the virus appears to be endemic.

Several publications have recently presented data showing immunological reactivity of selected synthetic peptides corresponding to antigenic proteins of HTLV-1. In one study several HTLV-1 gag peptides were synthesized. Palker et al., J. Immunology (1986) 136:2393-2397. One of the gag peptides designated SP-71, which corresponds to the C-terminus of the HTLV-1 p19 protein, was found to react with 8/9 HTLV-1 patient sera in a radioimmunoassay (RIA). The amino acid sequence of SP-71 is: Pro-Tyr-Val-Glu-Pro-Thr-Ala-Pro-Gln-Val-Leu. Copeland et al., J. Immunol. (1986) 137:6066-6098, synthesized three additional HTLV-1 peptides which correspond to regions of the protein product encoded by the env gene of HTLV-1. One of these peptides, SP-70, which is located near the C terminus of the major surface glycoprotein gp46, had antigenic activity but reacted with only 4/12 sera from HTLV-1 positive patients. Peptide SP-70 is encoded by the nucleotide sequence of the HTLV-1 genome encompassing base pairs 6066-6098 and has the amino acid sequence: Pro-Pro-Phe-Ser-Leu-Ser-Pro-Val-Pro-Thr-Leu-NH$_2$.

Synthetic peptides corresponding to regions of immunologically important proteins of HTLV-1 such as gp46 which would react with 100% efficiency with sera from HTLV-1 infected patients would find immediate use in diagnostic methods and as potential immunogenic compositions for eliciting the production of antibodies against HTLV-1.

SUMMARY OF THE INVENTION

In accordance with the present invention, four novel synthetic peptides corresponding to immunodominant regions of the envelope protein of HTLV-1 are provided which are useful in highly selective diagnostic methods for detecting HTLV-1 infections.

Novel synthetic peptides corresponding to immunodominant regions of the glycoprotein encoded by the HTLV-1 env gene have now been found. The peptides are useful for diagnosing ATL and TPS caused by HTLV-1 infection in suspected individuals and in methods for screening for exposure to HTLV-1 in blood and blood-derived products with a high degree of reliability and specificity.

The peptides can be used in methods of detecting antibodies to HTLV-1 in blood, serum or other test samples. The methods involve contacting the sample with at least one of the peptide antigens under conditions which allow an immunological complex to form between the peptide and any HTLV-1 specific antibodies which may be present in the sample. Measuring complex formation by suitable detection means indicates the presence or absence of antibodies to HTLV-1 in the sample.

The novel peptides may also be used in compositions to elicit the production in animals including man of specific antibodies against HTLV-1 antigens. Such compositions include vaccines for immunization against HTLV-1 infection.

The invention also encompasses methods for eliciting the production of antibodies against HTLV-1 antigens which involve administering at least one of the novel peptides to animals including man.

DESCRIPTION OF THE INVENTION

The present invention provides four peptides designated gpAHTLV-1, gpBHTLV-1, gpCHTLV-1 and gpHHTLV-1 which correspond to immunodominant regions of the envelope glycoprotein encoded by the env gene of HTLV-1 which have been synthesized and tested for immunoreactivity to HTLV-1 positive serum samples. The novel peptides are useful in tests to diagnose HTLV-1 infection or prior exposure to the virus and as immunogens in compositions to elicit the production in animals including man of antibodies against HTLV-1. The peptides encompassed by the invention comprise oligopeptides having amino acid sequences containing therein sequences which comprise continuous (linear) epitopes reactive with HTLV-1 specific antibodies.

The four peptides were selected from among eight different synthesized peptides designated A-H which correspond to the HTLV-1 envelope glycoprotein. These peptides were selected using various criteria similar to the selection of useful HIV-1 or HIV-2 peptides, e.g. proximity to or containing a cysteine residue (location of cysteine in similar proteins from related organisms being relatively invariant) and proximity to glycosylation sites. Although such criteria for selection of peptides can rule out potentially nonuseful peptides and indicate potentially useful peptides, further testing was required to identify which of the eight peptides would display immunoreactivity to HTLV-1 positive serum samples. The eight peptides were synthesized in the priority A through H with the F peptide believed to be least antigenic based on the above-criteria. Peptides D-F were not found to be reactive with known HTLV-1 positive sera; peptides A-C, and H designated gpAHTLV-1, gpBHTLV-1, gpCHTLV-1 and gpHHTLV-1 were found to be useful for diagnosis of HTLV-1 infection.

The invention thus encompasses the four immunologically reactive peptides and functionally equivalent variants thereof, which do not significantly affect the antigenic properties of the peptides, corresponding to regions of the envelope glycoprotein encoded by the env gene of HTLV-1. The peptides were synthesized by known solid phase peptide synthesis techniques. See e.g., Merrifield and Barany, *The Peptides: Analysis, Synthesis, Biology* (1980), vol. 1, Gross and Meinenhofer, eds., Academic Press, New York, Chap. 1. The synthesis also allows for one or two amino acids not corresponding to the original protein sequence to be added to the amino or carboxyl terminus of the peptides. Such extra amino acids are useful for coupling the peptides to each other, to another peptide, to a large carrier protein or to a solid support. Amino acids that are useful for these purposes include tyrosine, lysine, glutamic acid, aspartic acid, cysteine and derivatives thereof. Additional protein modification techniques may be used, e.g., $NH_2$-acetylation or COOH-terminal amidation, to provide additional means for coupling the peptides to another protein or peptide molecule or to a support.

The novel peptides corresponding to the HTLV-1 envelope glycoprotein sequences are set forth below:

gpAHTLV-1

X-Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Y-Z, wherein X is either a H of the amino terminal $NH_2$ group of the peptide or an additional amino acid bonded to the amino terminal $NH_2$ group of the peptide, the additional amino acid being selected to facilitate coupling of the peptide to a carrier protein or other carrier; Y is absent or Cys; and Z is OH or $NH_2$.

Peptide gpAHTLV-1 is encoded by the nucleotide sequence of the HTLV-1 genome encompassing base pairs (bp) 6342 through 6413 (numbering of Seiki et al., Proc. Natl. Acad. Sci. U.S.A. (1983) 80:3618–3622) which is in the region of the env gene. Peptide gpAHTLV-1 in which X is H, Y is Cys and Z is OH is particularly preferred.

gpBHTLV-1

The peptide gpBHTLV-1 corresponds to the region of the envelope protein encoded by about bp 6018–6086 of the HTLV-1 genome: X-Trp-Thr-His-Cys-Phe-Asp-Pro-Gln-Ile-Gln--Ala-Ile-Val-Ser-Ser-Pro-Cys-His-Asn-Ile-Leu-Y-Z, wherein X, Y, and Z have the same definitions as above. Peptide gpBHTLV-1 in which X is H, Y is Cys and Z is OH is particularly preferred.

gpCHTLV-1

The peptide gpCHTLV-1 corresponds to the region of the envelope protein encoded by about bp 5868–5930 of the HTLV-1 genome: X-Tyr-Thr-Cys-Ile-Val-Cys-Ile-Asp-Arg-Ala-Ser-Leu-Ser-Thr-Trp-His-Val-Leu-Tyr-Ser-Pro-Y-Z, wherein X, Y, and Z have the same definitions as above. Peptide gpCHTLV-1 in which X is H, Y is Cys and Z is OH is particularly preferred.

gpHHTLV-1

The peptide gpHHTLV-1 corresponds to the region of the envelope protein encoded by about base pairs 5727–5798 of the HTLV-1 genome: X-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Y-Z, wherein X, Y and Z have the same definition as above.

The peptides can be used in methods for detection of antibodies to HTLV-1 or HTLV-1 associated antigens. Preferably the methods which use the peptides to detect the presence of HTLV-1 specific antibodies in the sample involve contacting the sample with at least one of the peptides under conditions which allow the formation of an immunological complex between the peptide and any antibodies to HTLV-1 that may be present in the sample. The formation of an immunological complex, if any, indicating the presence of antibodies to HTLV-1 in the sample, is then detected and measured by suitable means.

Such methods include, inter alia, homogeneous and heterogeneous binding immunoassays, such as radioimmunoassays (RIA), ELISA and Western blot analyses. Further, the assay protocols using the novel peptides allow for competitive and non-competitive binding studies to be performed.

The peptides may be labeled (signal-generating) or unlabeled depending on the type of assay used. Labels which may be coupled to the peptides are those known in the art and include inter alia enzymes, radionuclides, fluorogenic and chromogenic substrates, cofactors, biotin/avidin, colloidal gold, and magnetic particles. Modification of the novel peptides, allows for coupling by known means to carrier proteins or peptides or to known supports, for example, polystyrene or polyvinyl microtiter plates, glass tubes or glass beads and chromatographic supports, such as paper, cellulose and cellulose derivates, and silica.

Preferred assay techniques, especially for large-scale clinical screening of patient sera and blood and blood-derived products are ELISA and Western blot techniques, ELISA tests being particularly preferred. The ELISA tests employing the peptides described above are based on those currently in use for detecting other antigens, e.g. tests to measure exposure to the AIDS virus which use human cell-derived, recombinant DNA-derived or synthesized antigenic proteins or portions thereof of HIV-1. For use as reagents in these assays, the peptides of the invention are conveniently bonded to the inside surface of microtiter wells. The peptides may be directly bonded to the microtiter well. It has been found, however, that maximum binding of the peptides to the wells is accomplished by pretreating the wells with polylysine prior to the addition of the peptides. Additionally, the novel peptides may be covalently attached by known means to a carrier protein, such as BSA, with the resulting conjugate being used to coat the wells. Generally the peptides were used in a concentration of between 10 to 100 μg/ml for coating, although as much as 500 μg/ml of a peptide may be required for the assay to be successful.

Samples are then added to the peptide coated wells where an immunological complex forms if antibodies to HTLV-1 are present in the sample. A signal generating means may be added to aid detection of complex formation. A detectable signal is produced if HTLV-1 specific antibodies are present in the sample.

The peptides of the invention may also be formulated into compositions, including vaccines, for use in eliciting production of antibodies in animals and man against HTLV-1. For formulation of such compositions, an immunogenically effective amount of at least one of the peptides gpAHTLV-1, gpBHTLV-1, gpCHTLV-1 and gpHHTLV-1 is admixed with a physiologically acceptable carrier suitable for administration to animals including man. The peptides may be covalently attached to each other, to other peptides, to a protein carrier or to other carriers, incorporated into liposomes or other such vesicles, or complexed with an adjuvant or adsorbent as is known in the vaccine art. Alternatively, the peptides are not complexed with the above and merely admixed with a physiologically acceptable carrier such as normal saline or a buffering compound suitable for administration to animals including man.

As with all immunogenic compositions for eliciting antibodies, the immunogenically effective amounts of the peptides of the invention must be determined. Factors to be considered include the immunogenicity of the native peptide, whether or not the peptide will be complexed with or covalently attached to an adjuvant or carrier protein or other carrier and route of administration for the composition, i.e. intravenous, intramuscular, subcutaneous, etc., and number of immunizing doses to be administered. Such factors are known in the vaccine art and it is well within the skill of immunologists to make such determinations without undue experimentation.

The invention is further illustrated by the following specific examples which are not intended in any way to limit the scope of the invention.

EXAMPLE 1

An Applied Biosystems peptide-synthesizer Model 430 A, was utilized for the synthesis of all of the peptides. Each synthesis used a p-methylbenzylhydrylamine solid phase support resin (Peptides International, Louisville, Ky.). The peptides were synthesized according to the *Users Manual for Peptide Synthesizer Model 430A*, Applied Biosystems, 1986.

All amino acids for use in synthesis contained t-butylcarbonyl groups (t-Boc) protecting the α-NH₂ group and were obtained from Novabiochem AG, Switzerland. Amino acids with reactive side chain groups contained additional protective groups to prevent unwanted and undesirable side chain reactions. The individual protected amino acids used in synthesizing all of the peptides are set forth in Table 1.

After completion of a particular synthesis, the protecting groups were removed from the synthesized peptide and the peptide was cleaved from the solid support resin by treatment at 0° C. with anhydrous hydrofluoric acid (HF) combining 10% anisole and 10% dimethylsulfide as scavenging agents. After cleavage, the HF in the sample was purged under a stream of $N_2$, with removal of any residual HF accomplished by subjecting the sample to vacuum at 0° C. The peptides were extracted from the resin by treatment with trifluoroacetic acid (TFA) which was then removed by evaporation at room temperature. Following TFA removal, the peptides were precipitated and washed with anhydrous ether.

Prior to use in specific assays, the peptides can be further purified, if desired, by reverse phase high performance liquid chromatography (HPLC). A particularly suited column for such purification is the reverse-phase Vydak® C-18 column using a water (TFA)—acetonitrile (TFA) gradient to elute the peptides.

TABLE 1

| Amino Acids Used in the Synthesis of Peptides |
|---|
| Boc—Ala—OH |
| Boc—Arg (Tos)—OH |
| Boc—Asn—OH |
| Boc—Asp (OBzl)—OH |
| Boc—Cys (pMeOBzl)—OH |
| Boc—Glu (OBzl)—OH |
| Boc—Gln—OH |
| Boc—Gly—OH |
| Boc—His(Tos)—OH |
| Boc—Ile—OH.½ H₂O |
| Boc—Leu—OH.H₂O |
| Boc—Lys (2-Cl—Z)—OH (cryst.) |
| Boc—Met—OH |
| Boc—Phe—OH |
| Boc—Pro—OH |
| Boc—Ser(Bzl)—OH.DCHA |
| Boc—Thr (Bzl)—OH |
| Boc—Trp (Formyl)—OH |
| Boc—Tyr(2-Br—Z)—OH |
| Boc—Val—OH |

Tos = Tosyl or p-Toluene sulfonic acid
oBzl = Benzyloxy
pMeoBzl = p-Methylbenzyloxy
2-Cl—Z = Carbobenzoxy chloride
2-Br—Z = Carbobenzoxybromide

EXAMPLE 2

Peptide gpAHTLV-1 having the amino acid sequence Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Cys-OH was synthesized as described in Example 1 and used in an ELISA test to measure its immunologic reactivity.

Polylysine at a concentration of 1 mg/ml was added to the microtiter plates and allowed to incubate for 30 minutes. The polylysine was then discarded and peptide gpAHTLV-1 was added to the wells in a concentration of 10 to 100 μg/ml for coating. After the peptide incubated in the well for a length of time sufficient to allow the peptide to become bonded to the well, the peptide solution was removed and a solution of glutaraldehyde, which stabilizes the peptide attachment to the wells, was added for 15 minutes. The glutaraldehyde solution was then removed, the wells washed with buffer, and a mixture of glycine and bovine serum albumin (BSA) was added which served to block unbound sites in the wells and minimize spurious reactions during the ELISA test per se. After a final washing step, the plates were ready to use. The prepared peptide-coated microtiter plates could be stored for several months without any decrease in antigenic activity of peptide gpAHTLV-1 coated on the wells.

A convenient variation of known ELISA methods was used with the microtiter plates prepared as above. Serum samples from individuals which had been diluted 1:50 in PBS (phosphate buffered saline) containing 0.05% polyoxyethylenesorbitan monolaurate (Tween 20) and 1% BSA were added to each well and allowed to incubate for 90 minutes at 37° C. in a humidified atmosphere. The diluted serum samples were then removed from the plates and the wells washed three times with PBS containing 0.05% Tween 20. A conjugated anti-human immunoglobulin (Ig) antibody was then added to the wells and allowed to incubate for 90 minutes. The conjugated antibody was produced in a goat or rabbit and was specific for human IgG, IgM, immunoglobulin light chains, or combinations thereof. Preferably, alkaline-phophatase conjugated anti-human IgG (from Dakopatts) diluted 1:500 for use in PBS containing 0.05% Tween 20 and 1% BSA was used in the ELISA. After the conjugate had incubated a sufficient length of time to react with bound human antibodies, the plates were washed three times as above. In order to detect antibodies to HTLV-1 in the human serum that react with the peptide gpAHTLV-1 used as the antigen, (i.e. positive reactions), a chromogenic substrate, alkaline phosphatase substrate (Sigma Cat. No. 104 tablets) dissolved in a Na carbonate/MgCl$_2$ buffer and adjusted to a concentration of 1 μg/ml which is cleaved by the alkaline phosphatase enzyme attached to the anti-human Ig antibody to yield a colored product, was added. After incubation for approximately 40 minutes at room temperature, positive reactions indicated the presence of antibodies in the sample reactive with the antigen. A yellow to orange to reddish-brown color in each well indicating a positive reaction, was read in a spectrophotometer at 405 nm to quantify the reaction. Spectrophotometric readings were adjusted to correct for background reactions.

EXAMPLE 3

Peptides gpAHTLV-1, gpBHTLV-1, gpCHTLV-1, synthesized as described in Example 1, were run in parallel ELISA tests as described in Example 2 against 6 serum samples positive for antibodies to HTLV-1, 8 serum samples positive for antibodies to HIV-1 and 10 blood donor sera negative for HIV-1/HIV-2. As shown in Table 2, 6/6 confirmed positive HTLV-1 serum samples reacted with peptide gpAHTLV-1, 5/6 confirmed positive sera reacted with gpBHTLV-1 and 5/6 confirmed positive sera reacted with gpCHTLV-1. The table also shows that none of the HIV-1 positive serum samples and none of the negative blood donor sera reacted with the peptides.

TABLE 2

Immunologic Reactivity Determined By ELISA Between Peptides gPAHTLV-1, gpBHTVL-1 and gpCHTLV-1 Antibodies in Sera Obtained From HTLV-1 Positive, HIV-1 Positive and Normal Donors

| Serum # | HTLV-1 WB* | Peptide | | |
|---|---|---|---|---|
| | | gpAHTLV-1 | gpBHTLV-1 | gpCHTLV-1 |
| 982 | + | 1.048** | 1.799** | 1.108** |
| 1048 | + | 2.074 | 2.029 | 0.750 |
| 1049 | + | 2.050 | 1.908 | 0.628 |
| 1050 | + | 2.105 | 2.309 | 0.758 |
| 1051 | + | 0.646 | 0.262 | 0.289 |
| 1052 | + | 1.862 | 2.173 | 2.344 |
| 951 (HIV1) | − | 0.072 | 0.048 | 0.084 |
| 840 (HIV1) | − | 0.111 | 0.092 | 0.079 |
| 952 (HIV1) | − | 0.114 | 0.050 | 0.095 |
| 845 (HIV1) | − | 0.226 | 0.199 | 0.191 |
| 847 (HIV1) | − | 0.104 | 0.069 | 0.116 |
| 849 (HIV1) | − | 0.202 | 0.115 | 0.113 |
| 949 (HIV1) | − | 0.048 | 0.053 | 0.082 |
| 950 (HIV1) | − | 0.090 | 0.058 | 0.090 |
| 39388 (BD) | − | 0.084 | 0.074 | 0.126 |
| 38389 (BD) | − | 0.097 | 0.090 | 0.092 |
| 39390 (BD) | − | 0.122 | 0.107 | 0.128 |
| 39391 (BD) | − | 0.119 | 0.095 | 0.178 |
| 39392 (BD) | − | 0.085 | 0.078 | 0.125 |
| 39393 (BD) | − | 0.096 | 0.082 | 0.050 |
| 39394 (BD) | − | 0.116 | 0.110 | 0.150 |
| 39395 (BD) | − | 0.109 | 0.075 | 0.079 |
| 39396 (BD) | − | 0.303 | 0.116 | 0.207 |
| 39397 (BD) | − | 0.142 | 0.077 | 0.108 |

= HIV1; HIV-1 positive sera
= BD; Blood donor sera (normal)
* = WB; Western Blot analyses
** = Spectrophotometric Readings, O.D.$_{405}$
cut off = Mean O.D.$_{405}$ of Negative Sera + 6 × S.D.
gpAHTLV-1 = 0.124 + 6 × 0.061 = 0.490 (O.D.$_{405}$)
gpBHTLV-1 = 0.088 + 6 × 0.035 = 0.298 (O.D.$_{405}$)
gpCHTLV-1 = 0.116 + 6 × 0.042 = 0.368 (O.D.$_{405}$)

EXAMPLE 4

Peptide gpHHTLV-1 having the amino acid sequence: Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH was synthesized as described in Example 1 and used in an ELISA test as described in Example 2 to measure its immunologic reactivity against confirmed Japanese HTLV-sera and sera from U.S.A. and Europe from patients with Adult T-cell Leukemia Tropical Spastic Paraparesis (TSP) and cerebrospinal fluids (CSF). As shown in Table 3, all known positive sera were confirmed HTLV-1 positive.

TABLE 3

| Sera | Positive in ELISA |
|---|---|

TABLE 3-continued

| | |
|---|---|
| Japanese HTLV-1 sera | 22/32 (69%) |
| ATL CSF | 1/1 |
| TSP sera | 4/4 |
| TSP CSF | 4/4 |

| True negative sera/CSF | Positive in ELISA |
|---|---|
| 28 blood donor sera | 0/28 |
| 30 HIV-1 positive sera | 0/30 |
| 8 HIV-2 positive sera | 0/8 |
| 4 Transplant recipients sera | 0/4 |
| 4 Leukemia patients sera | 0/4 |
| 4 EB virus IgM positive sera | 0/4 |
| 4 Rheumatoid factor positive sera | 0/4 |
| 8 CSF (aseptic meningitis) | 0/8 |

EXAMPLE 5

Absorbance values on Japanese HTLV-1 sera were measured in ELISA using gpHHTLV-1 as well as Du-Pont HTLV-1 ELISA and Western blot. All sera were diluted 1/50. The results are set forth in Table 4.

TABLE 4

| serum no. | Du-Pont HTLV-1 ELISA | Western blot | gpHHTLV-1 |
|---|---|---|---|
| 1247 | 0.815 | + | 0.472 |
| 1248 (neg) | 0.059 | − | 0.109 neg contr |
| 1249 | 1.605 | + | 0.026 |
| 1250 | 2.150 | + | 2.096 |
| 1251 | 1.896 | + | 0.276 |
| 1252 | 1.066 | + | 0.098 |
| 1253 | 0.917 | + | 0.206 |
| 1254 | 0.753 | + | 0.023 |
| 1255 | 1.511 | + | 0.606 |
| 1256 | 1.143 | + | 0.195 |
| 1257 | 1.708 | + | 1.713 |
| 1258 | 1.753 | + | 2.704 |
| 1259 | 1.790 | + | 1.455 |
| 1260 | 1.752 | + | 0.981 |
| 1261 | 1.795 | + | 0.920 |
| 1262 | 1.973 | + | 0.125 |
| 1263 | 1.994 | + | 0.058 |
| 1264 | 1.019 | + | 0.110 |
| 1265 | 1.590 | + | 1.385 |
| 1266 | 0.927 | + | 2.278 |
| 1267 | 1.946 | + | 0.782 |
| 1268 | 1.933 | + | 1.822 |
| 1269 | 1.377 | + | 1.013 |
| 1270 | 1.322 | + | 0.554 |
| 1271 | 1.253 | + | 0.076 |
| 1272 | 1.996 | + | 0.792 |
| 1273 | 1.907 | + | 2.426 |
| 1274 | 0.717 | + | 0.049 |
| 1275 | 2.044 | + | 0.730 |
| 1276 | 1.461 | + | 1.161 |
| 1277 | 1.802 | + | 0.224 |
| 1278 | 1.419 | + | 0.052 |
| 1279 | 0.781 | + | 0.061 |

EXAMPLE 6

Absorbance values on sera and CSF from patients with ATL and TSP were measured in ELISA using gpHHTLV-1 sera diluted 1/50, CSF sera was diluted 1/20. The results are set forth in Table 5.

TABLE 5

| sera/CSF | gpHHTLV-1 ELISA |
|---|---|
| neg blood donor sera | |
| 39511 | 0.045 |
| 39511 | 0.038 |
| 39512 | 0.015 |
| 39512 | 0.020 |
| 39513 | 0.020 |
| 39513 | 0.023 |

TABLE 5-continued

| sera/CSF | gpHHTLV-1 ELISA |
|---|---|
| neg CSF | |
| 8 | 0.033 |
| 19 | 0.039 |
| 21 | 0.056 |
| TSP/ATL sera | |
| TSP-BAR | 0.138 |
| TSP-SEPH | 0.226 |
| TSP-LER | 0.275 |
| TSP-SOR | 0.151 |
| ATL-SIE | 0.080 |
| ATL-LAUT | 0.077 |
| TSP/ATL CSF | |
| TSP-BAR | 0.275 |
| TSP-SEPH | 0.263 |
| TSP-LER | 0.369 |
| TSP-SOR | 0.418 |
| TSP-SIE | 0.027 |

It is evident from the foregoing results that the novel synthetic peptides, gpAHTLV-1, gpBHTLV-1, gpCHTLV-1 and gpHHTLV-1 described herein, which correspond to regions of the immunologically important envelope glycoprotein encoded by the env gene of HTLV-1, clearly provide unique reagents for a sensitive and selective assay for the presence of antibodies to HTLV-1.

We claim:

1. A peptide of the formula

X-Gly-Leu-Asp-Leu-Leu-Phe-Trp-Glu-Gln-Gly-
Gly-Leu-Cys-Lys-Ala-Leu-Gln-Glu-Gln-Cys-
Arg-Phe-Pro-Asn-Y-Z, wherein X is either a H of the amino terminal $NH_2$ group of the peptide or an additional amino acid bonded to the amino terminal $NH_2$ group of the peptide, the additional amino acid being selected to facilitate coupling of the peptide to a carrier protein; Y is absent or Cys; and Z is OH or $NH_2$.

2. A peptide of the formula

Gly-Leu-Asp-Leu-Leu-Phe-Trp-Glu-Gln-Gly-Gly-
Leu-Cys-Lys-Ala-Leu-Gln-Glu-Gln-Cys-Arg-
Phe-Pro-Asn-Cys-OH.

3. A peptide of the formula

X-Trp-Thr-His-Cys-Phe-Asp-Pro-Gln-Ile-Gln-Ala-
Ile-Val-Ser-Ser-Pro-Cys-His-Asn-Ile-Leu-Y-Z, wherein X is either a H of the amino terminal $NH_2$ group of the peptide or an additional amino acid bonded to the amino terminal $NH_2$ group of the peptide, the additional amino acid being selected to facilitate coupling of the peptide to a carrier protein; Y is absent or Cys; and Z is OH or $NH_2$.

4. A peptide of the formula

Trp-Thr-His-Cys-Phe-Asp-Pro-Gln-Ile-Gln-Ala-Ile-
Val-Ser-Ser-Pro-Cys-His-Asn-Ile-Leu-Cys-OH.

5. A peptide of the formula

X-Tyr-Thr-Cys-Ile-Val-Cys-Ile-Asp-Arg-Ala-Ser-
Leu-Ser-Thr-Trp-His-Val-Leu-Tyr-Ser-Pro-Y-Z, wherein X is either a H of the amino terminal $NH_2$ group of the peptide or an additional amino acid bonded to the amino terminal $NH_2$ group of the peptide, the additional amino acid being selected to facilitate coupling of the peptide to the carrier protein; Y is absent or Cys; and Z is OH or NH$_2$.

6. A peptide of the formula

Tyr-Thr-Cys-Ile-Val-Cys-Ile-Asp-Arg-Ala-Ser-Leu-Ser-Thr-Trp-His-Val-Leu-Tyr-Ser-Pro-Cys-OH.

7. A peptide of the formula

Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH.

8. A method for detecting antibodies to HTLV-1 in a sample comprising:
contacting the sample with at least one peptide selected from the group consisting of
X-Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Y-Z,
X-Trp-Thr-His-Cys-Phe-Asp-Pro-Gln-Ile-Gln-Ala-Ile-Val-Ser-Ser-Pro-Cys-His-Asn-Ile-Leu-Y-Z,
X-Tyr-Thr-Cys-Ile-Val-Cys-Ile-Asp-Arg-Ala-Ser-Leu-Ser-Thr-Trp-His-Val-Leu-Tyr-Ser-Pro-Y-Z and
X-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Y-Z,
wherein X is either a H of the amino terminal NH$_2$ group of the peptide or an additional amino acid bonded to the amino terminal NH$_2$ group of the peptide, the additional amino acid being selected to facilitate the coupling of the peptide to a carrier protein; Y is absent or Cys; and Z is OH or NH$_2$, under conditions such that an immunological complex will form between the peptide and antibodies to HTLV-1 if such antibodies are present in the sample and measuring the formation, if any, of the immunological complex to determine the presence of antibodies to HTLV-1 in the sample.

9. Method according to claim 8 in which the peptide is selected from the group consisting of
Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Cys-OH,
Trp-Thr-His-Cys-Phe-Asp-Pro-Gln-Ile-Gln-Ala-Ile-Val-Ser-Ser-Pro-Cys-His-Asn-Ile-Leu-Cys-OH,
Tyr-Thr-Cys-Ile-Val-Cys-Ile-Asp-Arg-Ala-Ser-Leu-Ser-Thr-Trp-His-Val-Leu-Tyr-Ser-Pro-Cys-OH and
Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH.

10. Method according to claim 8 in which the peptide is

Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Cys-OH.

11. Method according to claim 8 in which the peptide is

Trp-Thr-His-Phe-Asp-Pro-Gln-Ile-Gln-Ala-Ile-Val-Ser-Ser-Pro-Cys-His-Asn-Ser-Leu-Ile-Leu-Cys-OH.

12. Method according to claim 8 in which the peptide is

Tyr-Thr-Cys-Ile-Val-Cys-Ile-Asp-Arg-Ala-Ser-Thr-Trp-His-Cys-Val-Leu-Tyr-Ser-Pro-Cys-OH.

13. Method according to claim 8 in which the peptide is

Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH.

14. A composition for eliciting the production of antibodies against HTLV-1 infection in animals including man comprising an immunogenically effective amount of at least one peptide selected from the group consisting of
X-Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Y-Z,
X-Trp-Thr-His-Cys-Phe-Asp-Pro-Gln-Ile-Gln-Ala-Ile-Val-Ser-Ser-Pro-Cys-His-Asn-Ile-Leu-Y-Z,
X-Tyr-Thr-Cys-Ile-Val-Cys-Ile-Asp-Arg-Ala-Ser-Leu-Ser-Thr-Trp-His-Val-Leu-Tyr-Ser-Pro-Y-Z and
X-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Y-Z,
wherein X is either a H of the amino terminal NH$_2$ group of the peptide or an additional amino acid bonded to the amino terminal NH$_2$ group of the peptide, the additional amino acid being selected to facilitate the coupling of the peptide to a carrier protein; Y is absent or Cys; and Z is OH or NH$_2$, and a physiologically acceptable carrier.

15. Composition according to claim 14 in which the peptide is selected from the group consisting of
Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Cys-OH,
Trp-Thr-His-Cys-Phe-Asp-Pro-Gln-Ile-Gln-Ala-Ile-Val-Ser-Ser-Pro-Cys-His-Asn-Ile-Leu-Cys-OH,
Tyr-Thr-Cys-Ile-Val-Cys-Ile-Asp-Arg-Ala-Ser-Leu-Ser-Thr-Trp-His-Val-Leu-Tyr-Ser-Pro-Cys-OH and
Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH.

16. Composition according to claim 14 in which the peptide is

Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Cys-OH.

17. Composition according to claim 14 in which the peptide is

Trp-Thr-His-Cys-Phe-Asp-Pro-Gln-Ile-Gln-Ala-Ile-Val-Ser-Ser-Pro-Cys-His-Asn-Ile-Leu-Cys-OH.

18. Composition according to claim 14 in which the peptide is

Tyr-Thr-Cys-Ile-Val-Cys-Ile-Asp-Arg-Ala-Ser-Leu-Ser-Thr-Trp-His-Val-Leu-Tyr-Ser-Pro-Cys-OH.

19. Composition according to claim 14 in which the peptide is

Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH.

20. A method for eliciting the production of antibodies to HTLV-1 in animals including man comprising administering to animals including man an immunogenically effective amount of at least one peptide selected from the group consisting of X-Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Y-Z, X-Trp-Thr-His-Cys-Phe-Asp-Pro-Gln-Ile-Gln-Ala-Ile-Val-Ser-Ser-Pro-Cys-His-Asn-Ile-Leu-Y-Z, X-Tyr-Thr-Cys-Ile-Val-Cys-Ile-Asp-Arg-Ala-Ser-Leu-Ser-Thr-Trp-His-Val-Leu-Tyr-Ser-Pro-Y-Z and X-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Y-Z, wherein X is either a H of the amino terminal $NH_2$ group of the peptide or an additional amino acid bonded to the amino terminal $NH_2$ group of the peptide, the additional amino acid being selected to facilitate the coupling of the peptide to a carrier protein; Y is absent or Cys; and Z is OH or $NH_2$, and a physiologically acceptable carrier.

21. Method according to claim 20 in which the peptide is selected from the group consisting of Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Cys-OH, Trp-Thr-His-Cys-Phe-Asp-Pro-Gln-Ile-Gln-Ala-Ile-Val-Ser-Ser-Pro-Cys-His-Asn-Ile-Leu-Cys-OH, Tyr-Thr-Cys-Ile-Val-Cys-Ile-Asp-Arg-Ala-Ser-Leu-Ser-Thr-Trp-His-Val-Leu-Tyr-Ser-Pro-Cys-OH and Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH.

22. Method according to claim 20 in which the peptide is

Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Asn-Cys-OH.

23. Method according to claim 20 in which the peptide is

Trp-Thr-His-Cys-Phe-Asp-Pro-Gln-Ile-Gln-Ala-Ile-Val-Ser-Ser-Pro-Cys-His-Asn-Ile-Leu-Cys-OH.

24. Method according to claim 20 in which the peptide is

Tyr-Thr-Cys-Ile-Val-Cys-Ile-Asp-Arg-Ala-Ser-Leu-Ser-Thr-Trp-His-Val-Leu-Tyr-Ser-Pro-Cys-OH.

25. A peptide of the formula

X-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Y-Z, wherein X is either a H of the amino terminal $NH_2$ group of the peptide or an additional amino acid bonded to the amino terminal $NH_2$ group of the peptide, the additional amino acid being selected to facilitate the coupling of the peptide to a carrier protein; Y is absent or Cys; and Z is OH or $NH_2$.

26. Method according to claim 20 in which the peptide is

Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Cys-OH.

* * * * *

UNITED STATES PATENT AND TRADEMARK OFFICE
CERTIFICATE OF CORRECTION

PATENT NO. : 5,017,687                    Page 1 of 2
DATED      : May 21, 1991
INVENTOR(S): Vahlne et al.

It is certified that error appears in the above-identified patent and that said Letters Patent is hereby corrected as shown below:

Title Page, Item 75, lines 2 and 4, "Gothenburg" should read --Goteborg--;

Title Page, second column, line 17, "G ANtiobodies" should read --Antibodies--;

Col. 1, line 6, "07/166,255" should read --07/166,205--;

Col. 9, line 16, "phophatase" should read --phosphatase--;

Col. 10, line 2 of Table 2 heading, "gPAHTLV-1" should read --gpAHTLV-1--;

Col. 10, TABLE 2, line 13, "951(HIV1)" should read --951(HIV1)$^{\dagger}$--;

UNITED STATES PATENT AND TRADEMARK OFFICE
CERTIFICATE OF CORRECTION

PATENT NO. : 5,017,687

DATED : May 21, 1991

INVENTOR(S) : Vahlne et al.

It is certified that error appears in the above-identified patent and that said Letters Patent is hereby corrected as shown below:

Col. 10, TABLE 2, line 21, "39388(BD)" should read --39388(BD)$^{\dagger\dagger}$--;

Col. 10, TABLE 2, first line of footnotes, " = HIV1" should read --$\dagger$= HIV1--; and Col. 10, TABLE 2, second line of footnotes, " = BD" should read --$\dagger\dagger$=BD--.

Signed and Sealed this

Seventeenth Day of January, 1995

Attest:

BRUCE LEHMAN

*Attesting Officer*  *Commissioner of Patents and Trademarks*